(12) United States Patent
Malik et al.

(10) Patent No.: US 7,441,513 B1
(45) Date of Patent: Oct. 28, 2008

(54) PLASMA-GENERATED COATING APPARATUS FOR MEDICAL DEVICES AND A METHOD OF COATING DEPOSITION

(75) Inventors: Shamim M. Malik, Temecula, CA (US); Charles D. Claude, Sunnyvale, CA (US); Connie S. Kwok, Sunnyvale, CA (US); Michael Seegmiller, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 703 days.

(21) Appl. No.: 10/672,890

(22) Filed: Sep. 26, 2003

(51) Int. Cl.
C23C 16/00 (2006.01)
A61L 33/00 (2006.01)
B05D 3/00 (2006.01)
A61F 2/06 (2006.01)

(52) U.S. Cl. ............... 118/723 E; 118/723 I; 427/2.24; 623/1.46

(58) Field of Classification Search .......... 118/715; 427/488; 623/1.13, 1.46
See application file for complete search history.

(56) References Cited

U.S. PATENT DOCUMENTS

| 4,329,383 A | 5/1982 | Joh .................... 428/36 |
| 4,733,665 A | 3/1988 | Palmaz ................ 128/343 |
| 4,800,882 A | 1/1989 | Gianturco ............. 128/343 |
| 4,882,168 A | 11/1989 | Casey et al. .......... 424/468 |
| 4,886,062 A | 12/1989 | Wiktor ................ 128/343 |
| 4,941,870 A | 7/1990 | Okada et al. .......... 600/36 |
| 4,977,901 A | 12/1990 | Ofstead ............... 128/772 |
| 5,087,418 A * | 2/1992 | Jacob ................. 422/23 |
| 5,112,457 A | 5/1992 | Marchant ............. 204/165 |
| 5,165,919 A | 11/1992 | Sasaki et al. ......... 424/488 |
| 5,272,012 A | 12/1993 | Opolski .............. 428/423.1 |
| 5,292,516 A | 3/1994 | Viegas et al. ......... 424/423 |
| 5,298,260 A | 3/1994 | Viegas et al. ......... 424/486 |
| 5,300,295 A | 4/1994 | Viegas et al. ......... 424/427 |
| 5,306,501 A | 4/1994 | Viegas et al. ......... 424/423 |
| 5,328,471 A | 7/1994 | Slepian .............. 604/101 |
| 5,330,768 A | 7/1994 | Park et al. ........... 424/501 |
| 5,380,299 A | 1/1995 | Fearnot et al. ........ 604/265 |
| 5,417,981 A | 5/1995 | Endo et al. ........... 424/486 |
| 5,447,724 A | 9/1995 | Helmus et al. ........ 424/426 |
| 5,455,040 A | 10/1995 | Marchant ............. 424/426 |

(Continued)

FOREIGN PATENT DOCUMENTS

EP  0 301 856  2/1989

(Continued)

OTHER PUBLICATIONS

Anonymous, *Cardiologists Draw—Up The Dream Stent*, Clinica 710:15 (Jun. 17, 1996), http://www.dialogweb.com/cgi/document?reg=1061848202959, printed Aug. 25, 2003 (2 pages).

(Continued)

*Primary Examiner*—Parviz Hassanzadeh
*Assistant Examiner*—Rakesh K Dhingra
(74) *Attorney, Agent, or Firm*—Squire, Sanders & Dempsey L.L.P.

(57) ABSTRACT

An apparatus for plasma polymerize coating of medical devices, such as stents, is disclosed. A method for forming plasma-polymerized coating for implantable medical devices is also disclosed.

16 Claims, 11 Drawing Sheets

U.S. PATENT DOCUMENTS

| | | | | |
|---|---|---|---|---|
| 5,462,990 | A | 10/1995 | Hubbell et al. | 525/54.1 |
| 5,464,650 | A | 11/1995 | Berg et al. | 427/2.3 |
| 5,569,463 | A | 10/1996 | Helmus et al. | 424/426 |
| 5,578,073 | A | 11/1996 | Haimovich et al. | 623/1 |
| 5,591,268 | A * | 1/1997 | Usui et al. | 118/723 E |
| 5,605,696 | A | 2/1997 | Eury et al. | 424/423 |
| 5,609,629 | A | 3/1997 | Fearnot et al. | 623/1 |
| 5,624,411 | A | 4/1997 | Tuch | 604/265 |
| 5,628,730 | A | 5/1997 | Shapland et al. | 604/21 |
| 5,649,977 | A | 7/1997 | Campbell | 623/1 |
| 5,658,995 | A | 8/1997 | Kohn et al. | 525/432 |
| 5,667,767 | A | 9/1997 | Greff et al. | 424/9.411 |
| 5,670,558 | A | 9/1997 | Onishi et al. | 523/112 |
| 5,679,400 | A | 10/1997 | Tuch | 427/2.14 |
| 5,700,286 | A | 12/1997 | Tartaglia et al. | 623/1 |
| 5,702,754 | A | 12/1997 | Zhong | 427/2.12 |
| 5,716,981 | A | 2/1998 | Hunter et al. | 514/449 |
| 5,735,897 | A | 4/1998 | Buirge | 623/12 |
| 5,746,998 | A | 5/1998 | Torchilin et al. | 424/9.4 |
| 5,776,184 | A | 7/1998 | Tuch | 623/1 |
| 5,788,979 | A | 8/1998 | Alt et al. | 424/426 |
| 5,800,392 | A | 9/1998 | Racchini | 604/96 |
| 5,820,917 | A | 10/1998 | Tuch | 427/2.1 |
| 5,824,048 | A | 10/1998 | Tuch | 623/1 |
| 5,824,049 | A | 10/1998 | Ragheb et al. | 623/1 |
| 5,830,178 | A | 11/1998 | Jones et al. | 604/49 |
| 5,837,008 | A | 11/1998 | Berg et al. | 623/1 |
| 5,837,313 | A | 11/1998 | Ding et al. | 427/2.21 |
| 5,851,508 | A | 12/1998 | Greff et al. | 424/9.411 |
| 5,858,746 | A | 1/1999 | Hubbell et al. | 435/177 |
| 5,865,814 | A | 2/1999 | Tuch | 604/265 |
| 5,869,127 | A | 2/1999 | Zhong | 427/2.12 |
| 5,873,904 | A | 2/1999 | Ragheb et al. | 623/1 |
| 5,876,433 | A | 3/1999 | Lunn | 623/1 |
| 5,877,224 | A | 3/1999 | Brocchini et al. | 514/772.2 |
| 5,925,720 | A | 7/1999 | Kataoka et al. | 525/523 |
| 5,955,509 | A | 9/1999 | Webber et al. | 514/772.7 |
| 5,971,954 | A | 10/1999 | Conway et al. | 604/96 |
| 5,980,928 | A | 11/1999 | Terry | 424/427 |
| 5,980,972 | A | 11/1999 | Ding | 427/2.24 |
| 5,997,517 | A | 12/1999 | Whitbourne | 604/265 |
| 6,010,530 | A | 1/2000 | Goicoechea | 623/1 |
| 6,015,541 | A | 1/2000 | Greff et al. | 424/1.25 |
| 6,033,582 | A | 3/2000 | Lee et al. | 216/37 |
| 6,042,875 | A | 3/2000 | Ding et al. | 427/2.24 |
| 6,051,576 | A | 4/2000 | Ashton et al. | 514/255 |
| 6,051,648 | A | 4/2000 | Rhee et al. | 525/54.1 |
| 6,056,993 | A | 5/2000 | Leidner et al. | 427/2.25 |
| 6,060,451 | A | 5/2000 | DiMaio et al. | 514/13 |
| 6,060,518 | A | 5/2000 | Kabanov et al. | 514/781 |
| 6,080,488 | A | 6/2000 | Hostettler et al. | 428/423.3 |
| 6,096,070 | A | 8/2000 | Ragheb et al. | 623/1 |
| 6,099,562 | A | 8/2000 | Ding et al. | 623/1.46 |
| 6,110,188 | A | 8/2000 | Narciso, Jr. | 606/153 |
| 6,110,483 | A | 8/2000 | Whitbourne et al. | 424/423 |
| 6,113,629 | A | 9/2000 | Ken | 623/1.1 |
| 6,120,536 | A | 9/2000 | Ding et al. | 623/1.43 |
| 6,120,904 | A | 9/2000 | Hostettler et al. | 428/423.3 |
| 6,121,027 | A | 9/2000 | Clapper et al. | 435/180 |
| 6,129,761 | A | 10/2000 | Hubbell | 623/11 |
| 6,153,252 | A | 11/2000 | Hossainy et al. | 427/2.3 |
| 6,165,212 | A | 12/2000 | Dereume et al. | 623/1.13 |
| 6,203,551 | B1 | 3/2001 | Wu | 606/108 |
| 6,231,600 | B1 | 5/2001 | Zhong | 623/1.42 |
| 6,240,616 | B1 | 6/2001 | Yan | 29/527.2 |
| 6,245,753 | B1 | 6/2001 | Byun et al. | 514/56 |
| 6,251,136 | B1 | 6/2001 | Guruwaiya et al. | 623/1.46 |
| 6,254,632 | B1 | 7/2001 | Wu et al. | 623/1.15 |
| 6,258,121 | B1 | 7/2001 | Yang et al. | 623/1.46 |
| 6,283,947 | B1 | 9/2001 | Mirzaee | 604/264 |
| 6,283,949 | B1 | 9/2001 | Roorda | 604/288.02 |
| 6,284,305 | B1 | 9/2001 | Ding et al. | 427/2.28 |
| 6,287,628 | B1 | 9/2001 | Hossainy et al. | 427/2.3 |
| 6,299,604 | B1 | 10/2001 | Ragheb et al. | 604/265 |
| 6,306,176 | B1 | 10/2001 | Whitbourne | 623/23.59 |
| 6,331,313 | B1 | 12/2001 | Wong et al. | 424/427 |
| 6,335,029 | B1 | 1/2002 | Kamath et al. | 424/423 |
| 6,346,110 | B2 | 2/2002 | Wu | 606/108 |
| 6,358,556 | B1 | 3/2002 | Ding et al. | 427/2.24 |
| 6,379,381 | B1 | 4/2002 | Hossainy et al. | 623/1.42 |
| 6,395,326 | B1 | 5/2002 | Castro et al. | 427/2.24 |
| 6,419,692 | B1 | 7/2002 | Yang et al. | 623/1.15 |
| 6,451,373 | B1 | 9/2002 | Hossainy et al. | 427/2.25 |
| 6,494,862 | B1 | 12/2002 | Ray et al. | 604/96.01 |
| 6,503,556 | B2 | 1/2003 | Harish et al. | 427/2.24 |
| 6,503,954 | B1 | 1/2003 | Bhat et al. | 514/772.2 |
| 6,504,307 | B1 * | 1/2003 | Malik et al. | 315/111.21 |
| 6,506,437 | B1 | 1/2003 | Harish et al. | 427/2.25 |
| 6,527,801 | B1 | 3/2003 | Dutta | 623/1.46 |
| 6,527,863 | B1 | 3/2003 | Pacetti et al. | 118/500 |
| 6,540,776 | B2 | 4/2003 | Sanders Millare et al. | 623/1.15 |
| 6,544,223 | B1 | 4/2003 | Kokish | 604/103.01 |
| 6,544,543 | B1 | 4/2003 | Mandrusov et al. | 424/422 |
| 6,544,582 | B1 | 4/2003 | Yoe | 427/2.24 |
| 6,555,157 | B1 | 4/2003 | Hossainy | 427/2.24 |
| 6,558,733 | B1 | 5/2003 | Hossainy et al. | 427/2.24 |
| 6,565,659 | B1 | 5/2003 | Pacetti et al. | 118/500 |
| 6,572,644 | B1 | 6/2003 | Moein | 623/1.11 |
| 6,585,765 | B1 | 7/2003 | Hossainy et al. | 623/1.45 |
| 6,585,926 | B1 | 7/2003 | Mirzaee | 264/400 |
| 6,605,154 | B1 | 8/2003 | Villareal | 118/500 |
| 7,247,338 | B2 * | 7/2007 | Pui et al. | 427/2.24 |
| 2001/0018469 | A1 | 8/2001 | Chen et al. | 523/121 |
| 2001/0037145 | A1 | 11/2001 | Guruwaiya et al. | 623/1.15 |
| 2002/0077693 | A1 | 6/2002 | Barclay et al. | 623/1.13 |
| 2002/0091433 | A1 | 7/2002 | Ding et al. | 623/1.2 |
| 2002/0155212 | A1 | 10/2002 | Hossainy | 427/2.25 |
| 2003/0065377 | A1 | 4/2003 | Davila et al. | 623/1.13 |
| 2003/0099712 | A1 | 5/2003 | Jayaraman | 424/486 |

FOREIGN PATENT DOCUMENTS

| | | |
|---|---|---|
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 273 314 | 1/2003 |
| GB | 2287473 A * | 9/1995 |
| JP | 2001-190687 | 7/2001 |
| WO | WO 91/12846 | 9/1991 |
| WO | WO 95/10989 | 4/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/17331 | 4/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |

| | | |
|---|---|---|
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |

OTHER PUBLICATIONS

Anonymous, *Heparin-coated stents cut complications by 30%*, Clincia 732:17 (Nov. 18, 1996), http://www.dialogweb.com/cgi/document?reg=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?reg=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 262A (Abstract) (Feb. 1989).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Inou et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials For Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, European Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjugate Chemistry 11(2):131-139 (Mar./Apr. 2000).

Peng et al., *Role of polymers in improving the results of stenting in coronary arteries*, Biomaterials 17:685-694 (1996).

Shigeno, *Prevention of Cerebrovascular Spasm By Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

\* cited by examiner

PLASMA-GENERATED COATING APPARATUS FOR MEDICAL DEVICES AND A METHOD OF COATING DEPOSITION

BACKGROUND

1. Field of the Invention

This invention relates to an apparatus for fabricating plasma-generated coatings for medical devices such as stents. The invention also relates to method of coating such devices.

2. Background

Figure 1:
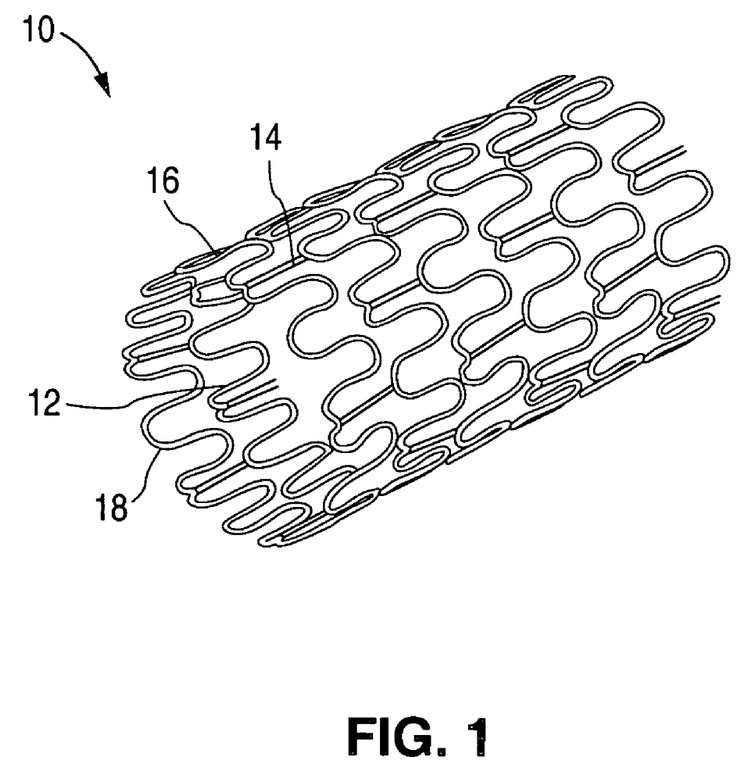
FIG. 1 illustrates a conventional stent.

Stents act as scaffoldings, functioning to physically hold open and, if desired, to expand the wall of the passageway. Stents are usually compressible, so that they can be inserted through small cavities via catheters, and then expanded to a larger diameter once they are at the desired location. FIG. 1 illustrates one example of a conventional vascular stent 10. The stent 10 includes struts 12 connected by elements 14. The combination of the struts 12 and the elements 14 define a tubular body of the stent 12. The tubular body has an outer surface 16 and an inner surface 18. Although the rate of restenosis has been reduced by mechanical intervention of stents, restenosis still presents a significant medical problem. Accordingly, stents have been modified to function not only as mechanical scaffolding, but also to provide biological therapy.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results.

One conventional method of medicating a stent involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent strut surfaces a coating of the polymer and the therapeutic substance impregnated in the polymer.

One of the drawbacks and disadvantages associated with the use of medicated stents has been the aggregation of platelets on the device. A high degree of such aggregation, combined with the early onset of monocyte activation, is believed to be a factor leading to restenosis. One way to reduce platelet aggregation, as well as the early onset of monocyte activation, is believed to be by forming the stent coating using the process of plasma polymerization. Plasma polymerization, also known as glow discharge polymerization, is a method of polymerizing organic substances from vapor phase at low pressures. Plasma polymerization is generally performed by introducing a gas including one or more monomers into a vacuum zone in which the substrate to be coated is placed. The polymerizable monomers are then subjected to an electric discharge to generate ions and/or free radicals. While plasma polymerization can produce coatings having good properties, improvements in the quality of the coatings is desired. For instance, due to the harsh conditions existing in the plasma environment, some areas of the plasma-formed stent coatings can include defects such as burn marks, excessive roughness, and sometimes even delamination. It is desirable to eliminate or at least minimize these problems. Additionally, existing plasma polymerization technologies allow coating of only one stent at a time. To increase production of drug eluting stents, it is desirable to be able to form a plasma polymerized coating on many stents simultaneously. The embodiments of the present invention address these and other issues associated with coating of implantable medical devices.

SUMMARY

An apparatus to plasma coat a stent, is disclosed, comprising a mandrel supporting a stent; a first plasma member circumscribing the mandrel, the first plasma member being grounded; a second plasma member circumscribing the first plasma member; and a plasma generating source in communication with the second plasma member. In one embodiment, the first plasma member is a first hollow tubular body in which the mandrel is positioned, and the second plasma member is a second hollow tubular body in which the first hollow tubular body is positioned. The first and second hollow tubular bodies can include perforations or have a screen or mesh-like body. In accordance with another embodiment, the first plasma member is a hollow tubular body in which the mandrel is positioned and the second plasma member is a coil element wrapped around the first tubular body. The plasma generating source can be a radio frequency generating source or a microwave generating source. The apparatus can also include a first plate member in communication with the first plasma member; a second plate member positioned over the first plate member and in commutation with the second plasma member; and an insulator disposed between the first and second plate members to electrically insulate the plate members. The mandrel can extend from the first plate member into the first plasma element.

An apparatus to coat an implantable medical device, is provided comprising a first tubular member; a second tubular member in which an implantable medical device can be placed, the second tubular member being positioned within the first tubular member and the second tubular member being electrically isolated from the first tubular member; and an energy source in communication with the first tubular member. The tubular members can include bodies having holes disposed therein. The energy source can be configured to create plasma within the first tubular body. The second tubular body can be coupled to a ground source.

A method of forming a coating for an implantable medical device is also provided using the aforementioned devices.

DETAILED DESCRIPTION

Apparatus

FIGS. 2-6 illustrate a plasma polymerization apparatus 20, in accordance with embodiments of the invention, that can be placed within a pressure controlled plasma chamber 22. The apparatus 20 can be spherical in design and can include an upper plate member 24, a middle plate member 26 and a lower plate member 28. The plate members 24, 26 and 28 can have a general diameter of about 5 to about 6 inches (about 127 mm to 152 mm) and can each have a thickness of about 0.25 about 0.5 inch (about 6 mm to 12 mm). The plate members 24, 26, and 28 can be made of any suitable conductive material such as stainless steel or aluminum. Each member 24, 26, and 28 can be made of the same material or different materials.

The middle plate member 26 and the lower plate members 28 are positioned in close proximity to one another. The distance between the middle plate member 26 and the lower plate 28 can be, for example, about 0.125 to about 0.375 inch (about 3 to 9 mm). The total height of the apparatus 20, measured as the distance between the upper surface of the plate member 24 and the lower surface of the plate member 28, can be between about 3 to 6 inches (about 75 to 150 mm). The plate members 26 and 28 are separated by insulating material 30, such a ceramic material, an example of which can be alumina ($Al_2O_3$). The lower plate member 28 can be grounded.

Figure 3:
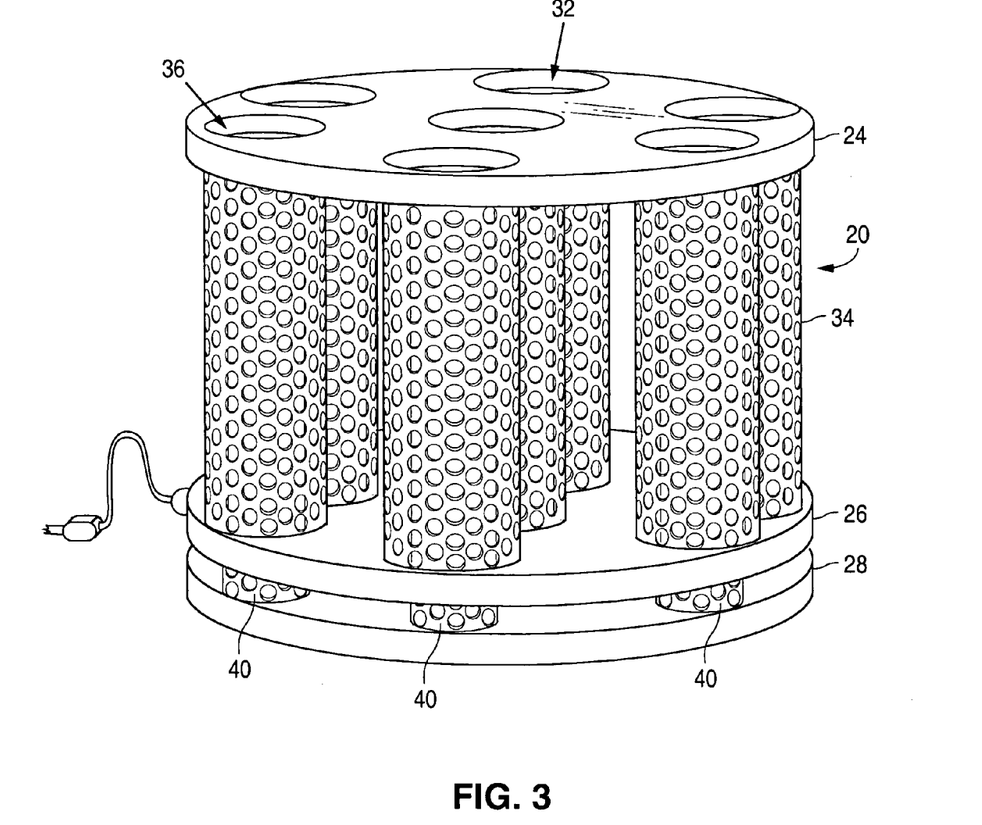
FIG. 3 is a perspective view of the plasma polymerization apparatus in accordance with one embodiment of the invention.
Figure 4:
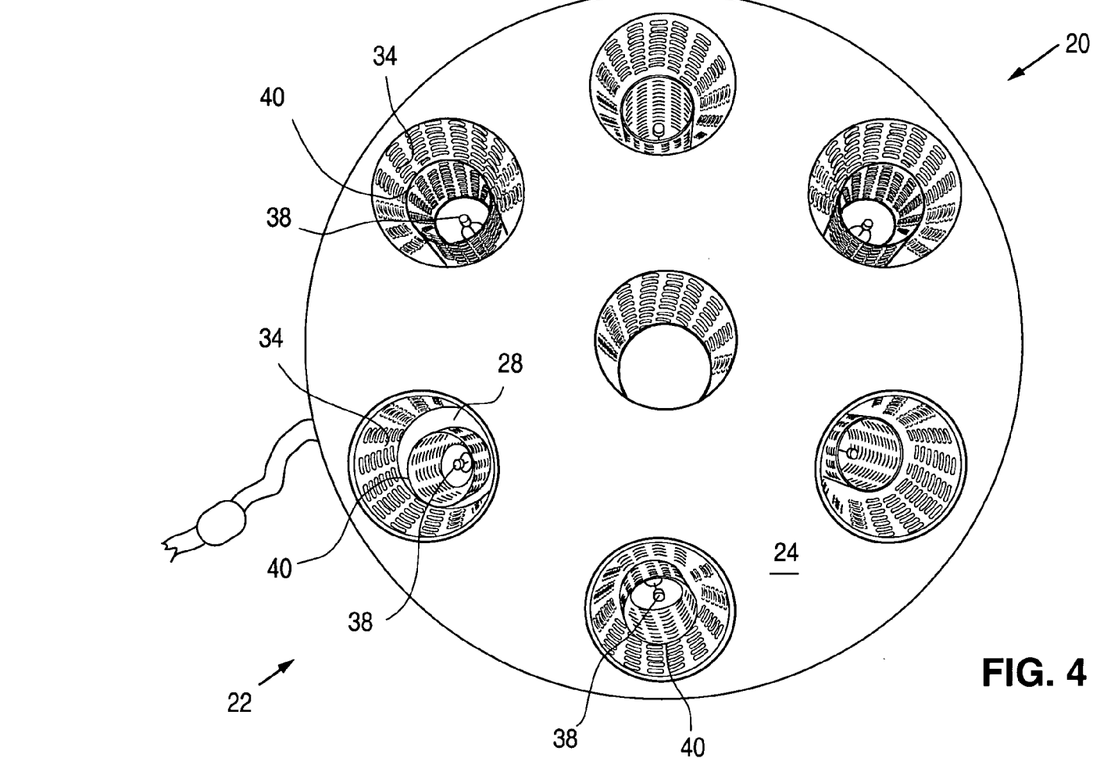
FIG. 4 is a top view of the apparatus of FIG. 3.

A plurality of plasma regions or cavities 32 are disposed between the upper plate member 24 and the middle plate member 26. Referring to FIGS. 3 and 4, the plasma cavities 32 are defined by the space created within first plasma elements or outer screens 34. The outer screens 34 can be made of a metal, such as stainless steel, or alternatively, titanium or aluminum. The outer screens 34 can be made of solid metal tubular sheets, but preferably are mesh-like or perforated as shown by FIGS. 3 and 4. It its believed that perforation of the screens 34 provides a plasma generated coating with better uniformity and better physical and mechanical properties. The total area covered by perforation can be about 64% of the surface of the screen 34. The diameter of the perforations can be from about 0.25 to about 0.375 inch (about 3 to 9 mm), for example about 0.3 inch (about 7.5 mm). The inner diameter of each of the screens 34 is between about 1 to 2 inches (about 25 to 50 mm). As illustrated by FIGS. 3 and 4, the upper plate member 24 can include circular openings 36 at the top of each of the tubular screens 34. As best illustrated by the figures, the middle plate member 26 includes respective openings for allowing mandrels 38, for supporting the stents, to extend from the lower plate 28 into the plasma cavities 32.

As illustrated in FIG. 4, second plasma elements or inner screens 40, similar to that of the outer screens 34 but of smaller diameter, are positioned within the outer screens 34. The inner screens 40 and the outer screens 34 are positioned concentrically; however, a slight (~5-10%) deviation from the concentricity is acceptable, although not preferred. The inner screens 40 are also made of a metal, such as stainless steel, or alternatively, titanium or aluminum. The inner screens 40 can also be made of a solid tubular metal sheet, but preferably are perforated or mesh-like as well. Perforations allow a better access of radicals and ions generated by plasma to the central area of cavities 32. The total area covered by perforation can be about 64% of the surface of the inner screen 40. The diameter of the inner screen 40 can be about 0.5 to 1 inch (about 12.5 to 25 mm).

The upper and middle plates 24 and 26 and the outer screens 34 are in electric communication with one another as to form an electric circuit. To generate plasma, a radio-frequency (RF) signal can be directed to the upper 24 or middle plate 26. By way of example, a radio frequency source such as Cesar® 133, 300 W unit, manufactured by Dressler of Germany can be used. Alternatively, instead of using the RF signal, plasma-can be generated using a microwave source, or any other suitable source known to those having ordinary skill in the art.

It is desirable that the plasma exist only within the space defined by cavities 32 but not outside this space. It is also desirable to avoid arcing to the stent surface and eliminate dielectric break down of the substrate film. In order to insure that the plasma will exist only within the space defined by cavities 32 (which includes the space inside the inner screens 40), as well as to avoid arcing to the stent surface and eliminate dielectric break down of the substrate film, the inner screens 40 are grounded by being in communication with the bottom plate 28. The inner screen 40 and the mandrel 38 are not seen in the central cavity of the apparatus shown by FIG. 4, but in fact the inner screen 40 and the mandrel 38 can also be used in this central cavity. The inner screen 40 and the mandrel 38 for the central cavity are provided on the chamber 22, and the inner screen 40 and mandrel 38 are inserted in the central cavity when the apparatus of FIG. 4 is placed in the chamber 22.

The mandrels 38, for supporting stents, extend from the lower plate 28 through the openings of the middle plate 26 and into the plasma cavities 32. The mandrels 38 do not make contact with the middle plate 26. For better quality and uniformity of the coating, the mandrels 38 and the stents are preferably positioned in the center of the cavities 32 (i.e., in the center of inner as well as outer screens 34 and 40); however, positioning the mandrels 38 and the stents between about 5 to 10% off center is acceptable, but not preferred. The mandrels 38 should support the stents without the stents contacting the inner screen 40. The mandrels are made of stainless steel and are also grounded.

Figure 5:
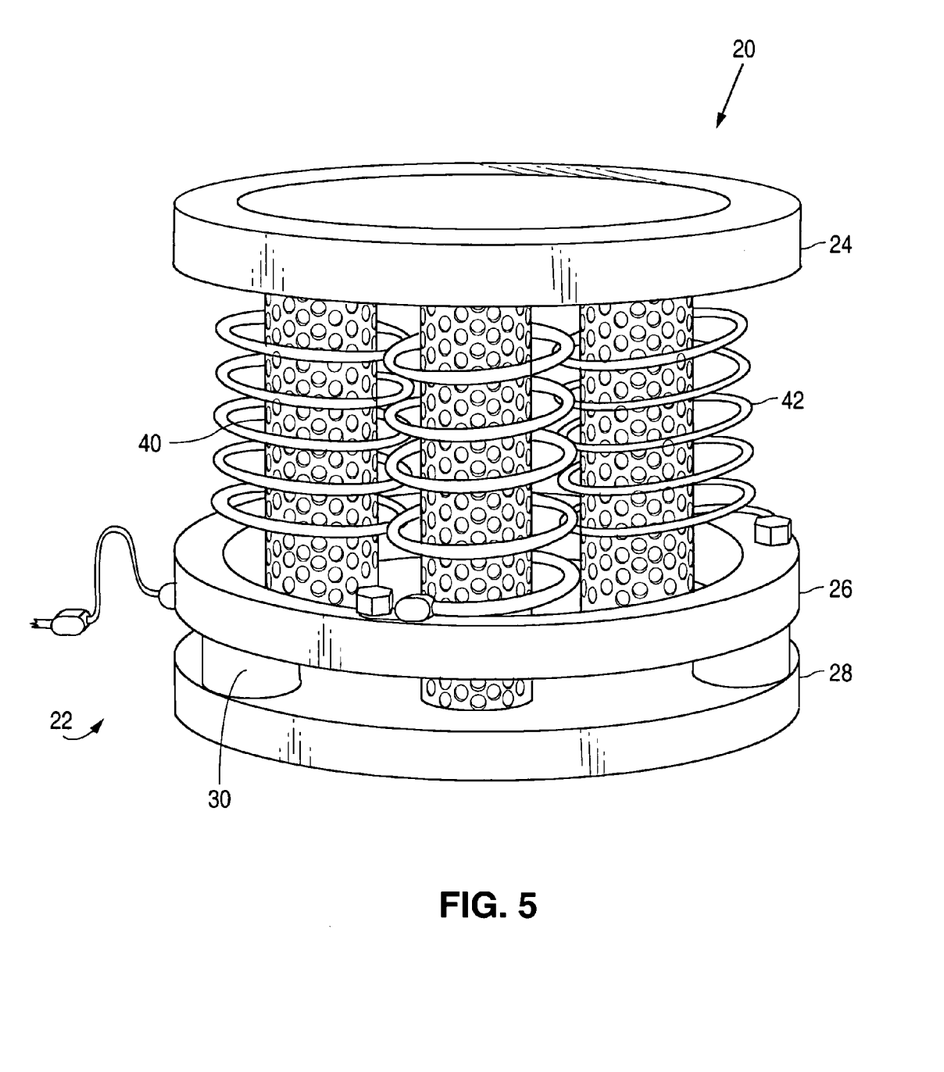
FIG. 5 is a side view of a plasma polymerization apparatus according to another embodiment of the invention.
Figure 6:
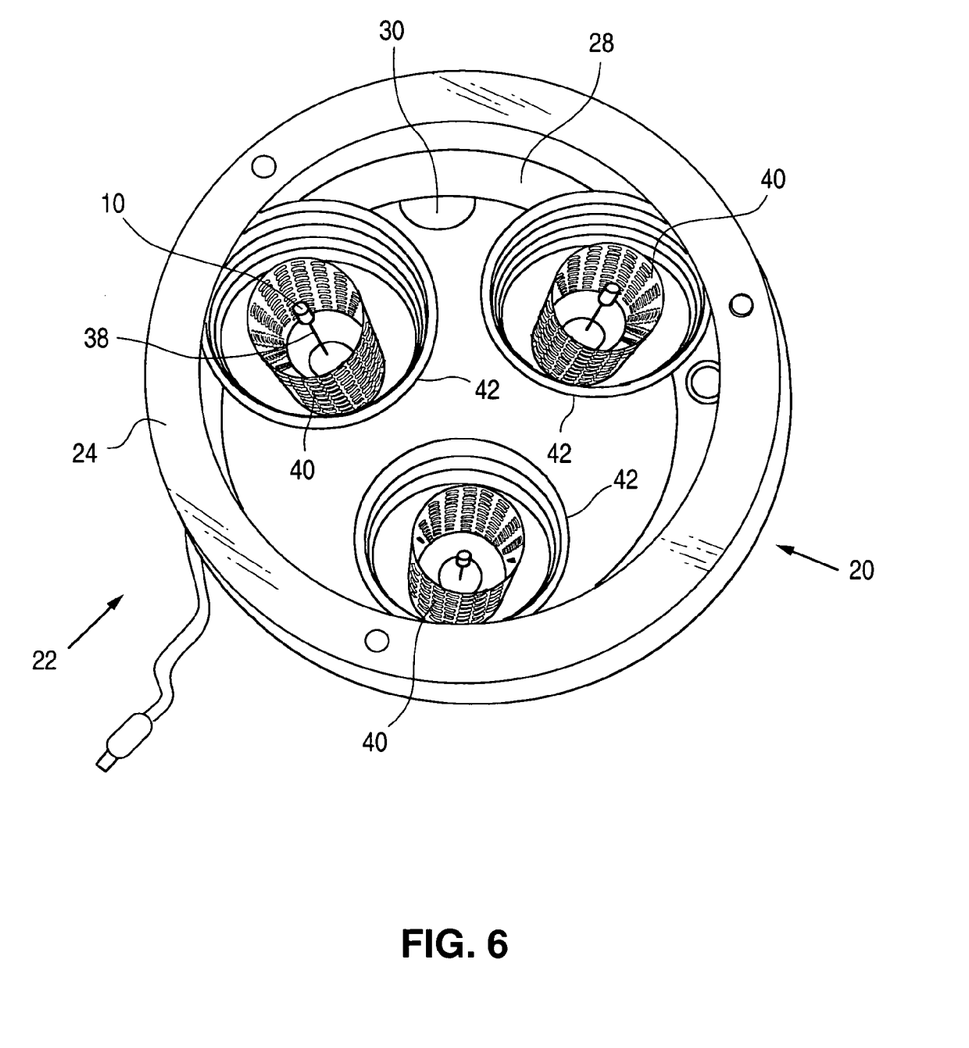
FIG. 6 is a top view of the apparatus of FIG. 5.
Figure 7:
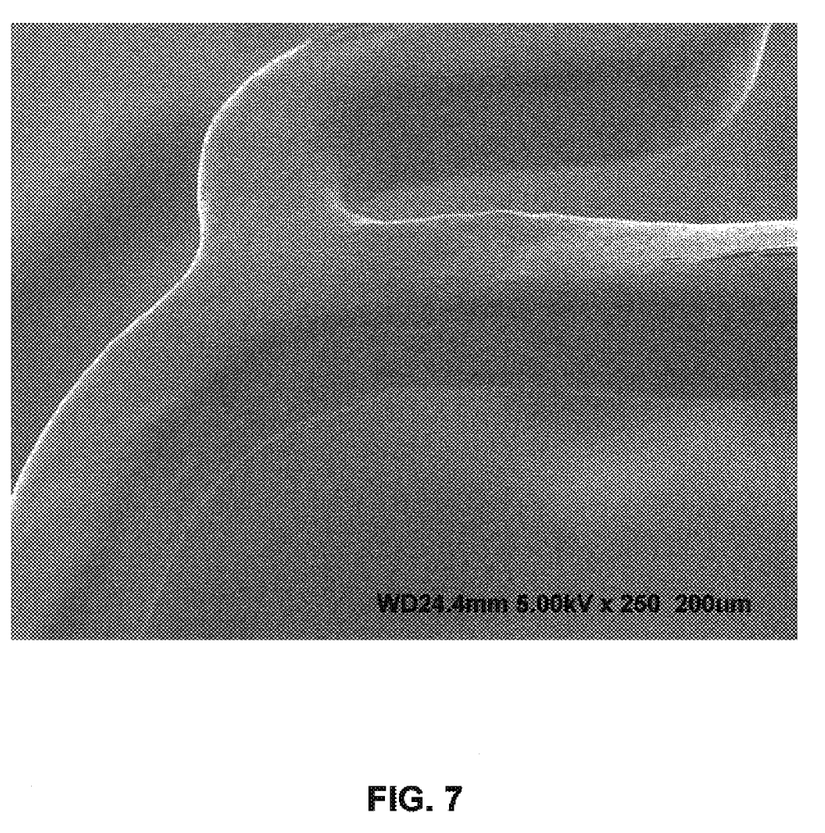
FIGS. 7-10 are microphotographs of various areas of a stent coating made according to an embodiment of the present invention.
Figure 8:
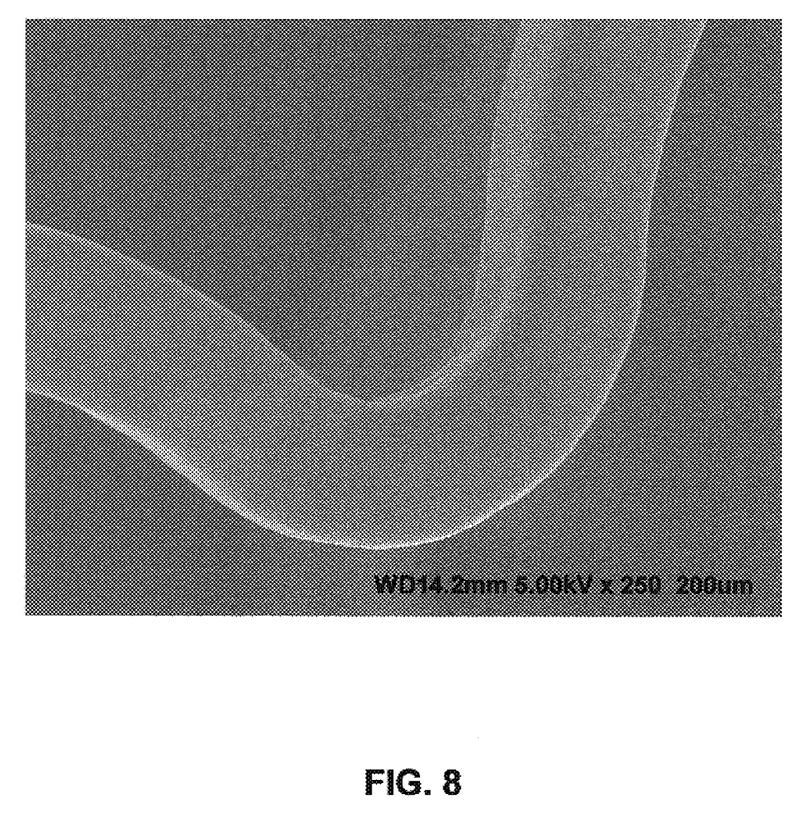
Figure 9:
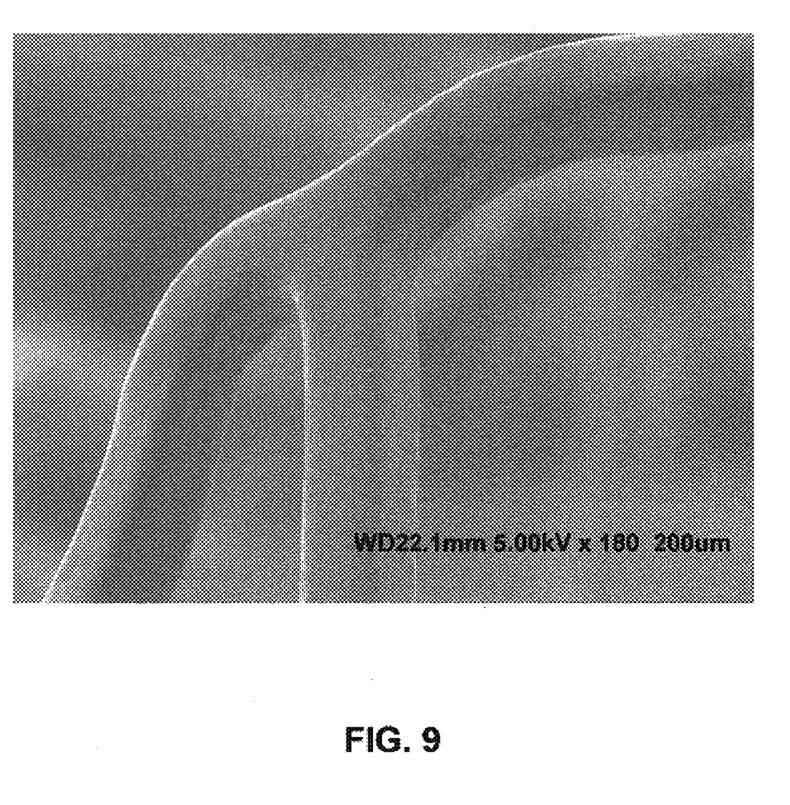
Figure 10:
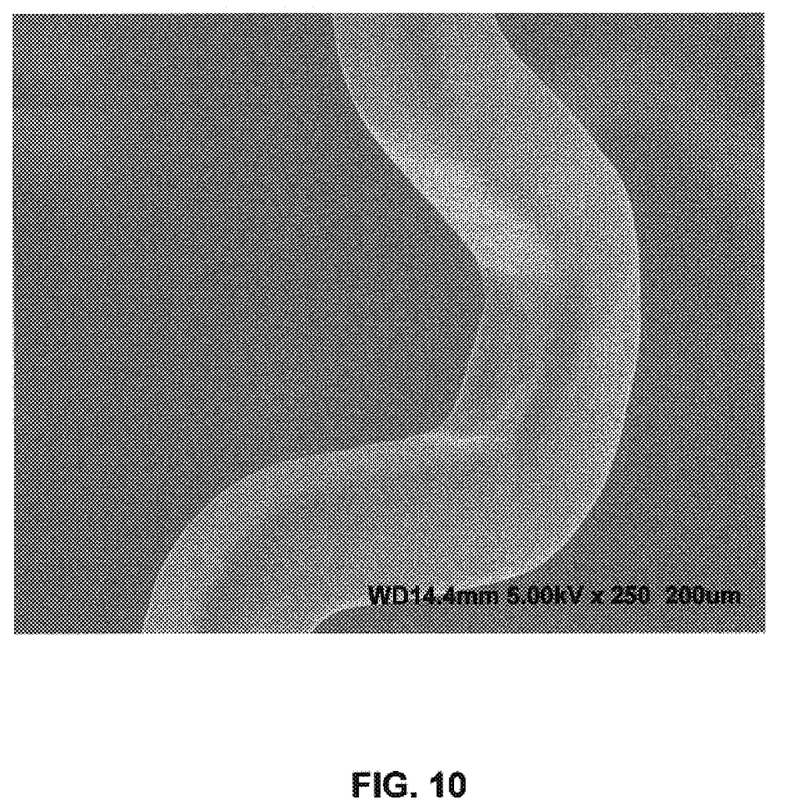

In accordance to another embodiment, as illustrated by FIGS. 5 and 6, in lieu of perforated outer screens 34, coils 42 wrapped around the grounded inner tubular perforated screens 40, can be used to generate the plasma. The coils 42 can be coupled to the upper 24 or middle 26 plate member. The coils 42 can be wrapped around the inner screens 40 any suitable number of times (e.g., 4 to 8) and can include an inner spatial diameter of about 1 to 2 inches (about 25 to 50 mm). The coils 42 can be made from stainless steel and can have a coil diameter of about 1.5 to 2 inches (about 37 to 50 mm).

Method of Coating

Any portion of the outer surface 16 of the stent 10 can be modified using gaseous plasma according to embodiments of the present invention. The surface modification includes formation of a polymer film on the surface 16 of the stent 10, the polymer film formed as a result of the process of plasma-induced polymerization of monomer(s), oligomer(s), or pre-polymer(s). A polymerizable monomer gas can be introduced into the plasma chamber, and the RF field can be applied to induce polymerization of the monomer on the surface 16 of the stent 10 to form the polymer film, i.e., a "plasma-polymerized film." The surface modification is not intended to be limited to any particular region of the outer surface 16 of the stent 10.

Examples of polymerizable monomeric gases that can be used to deposit a plasma-polymerized film on the surface 16 of the stent 10 include fluorinated compounds such as fluorinated alkanes, fluorinated alkenes, and their derivatives, for example, vinylidene fluoride (VDF), 1,2-difluoroethane, tetrafluoroethylene, or hexafluoropropene (HFP), or mixtures thereof.

Figure 2:
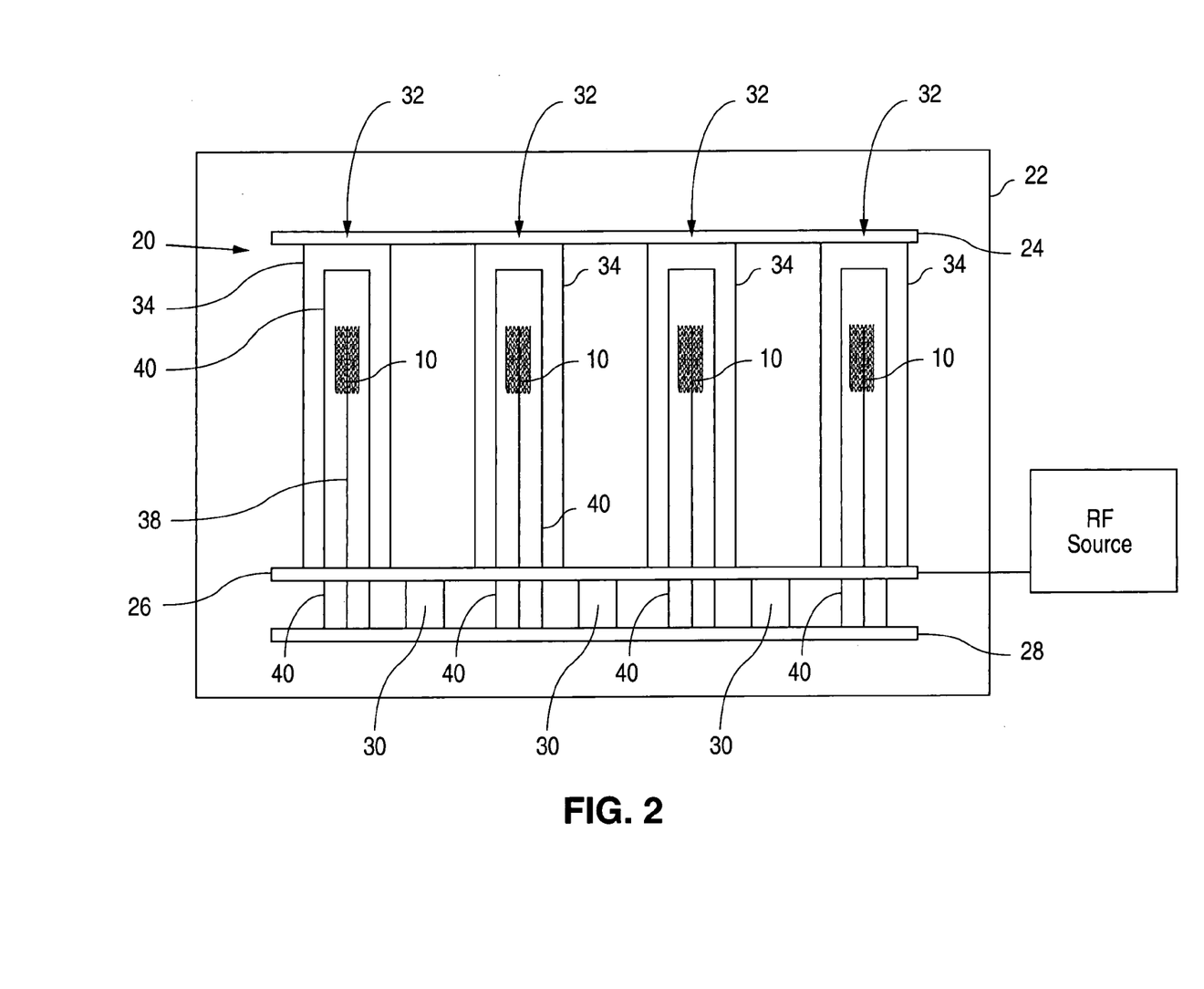
FIG. 2 is a schematic view of a plasma polymerization apparatus for housing implantable medical devices during polymerization process.

In addition, some non-fluorinated compounds, such as alkenes, (meth)acrylates, and glycol-like monomers (glymes) can be used. Some examples of suitable (meth)acrylates include acrylic acid (AA), butyl methacrylate (BMA), or 2-hydroxyethyl methacrylate (HEMA). With AA, carbon dioxide can also be added to the feed mixture introduced into the chamber 22. Examples of alkenes include ethylene or propylene. Examples of glycol-like monomers include diglyme, triglyme or ethylene oxide.

If VDF is used to form a polymer on the surface 16 of the stent 10, it is known that under plasma conditions, a multi-step process occurs, whereby VDF having the formula $CH_2=CF_2$ fragments into methylene radicals ($:CH_2$) and difluoromethylene radicals ($:CF_2$) along with various other decomposition products such as ($:CH.$) and ($H.$), followed by the recombination thereof. Among possible paths of such recombination is a reaction between only the methylene radical species (reaction I) or a reaction between one methylene radical and one difluoromethylene radical species (reaction II):

$$(n/2):CH_2+(n/2):CH_2 \rightarrow -[CH_2-CH_2]_n- \qquad (I)$$

$$(m/2):CH_2+(m/2):CF_2 \rightarrow -[CH_2CF_2]_m-, \qquad (II)$$

where "n" and "m" are integers. Another possible path can lead to recombination of difluoromethylene radicals to form some amount of poly(vinylidene fluoride)(PVDF) on the stent surface.

The process of polymerization predominantly follows reaction path (I) at lower pressures (less than about 30 mTorr, for instance, about 20 mTorr) leading to formation of mostly poly(ethylene)-like polymer on the surface 16 of the stent 10. At higher pressures (above about 80 mTorr, for example, about 90 mTorr), due to the formation of difluoromethylene radical species, reaction (II) predominantly occurs, where recombination takes place equally between fluorinated and protonated methylene species. As a result, at higher pressures (>60 mTorr) mostly a poly(vinylidenefluoride)(PVDF)-like polymer is obtained.

VDF can be introduced into the plasma chamber at a flow rate of about 45-60 sccm, followed by introduction of argon into the plasma chamber. Argon plasma can be then initiated by applying the RF power of about 60 W to cause the formation of the polymer coating on the surface 16 of the stent 10. The time needed for plasma-induced polymerization can be between about 2 to 15 minutes. The plasma is then turned off by terminating the RF power.

If acrylic acid (AA) is used to form a polymer on the surface 16 of the stent 10, the parameters which can be used to conduct the process of plasma-induced polymerization are reflected in Table 1.

TABLE 1

| Process Parameters | Parameter Range | Exemplary Value |
|---|---|---|
| carbon dioxide flow rate (sccm) | 60 to 200 | 90 |
| acrylic acid flow rate (ml/min) | 0.05 to 0.35 | 0.2 |
| pressure (mTorr) | 70 to 250 | 150 |
| RF power (W) | 50 to 250 | 100 |
| RF frequency (MHz) | 2 to 2800 | 13.54 |
| power/flow rate (MJ/Kg) | 9 to 35 | 13.7 |

The thickness of the plasma-polymerized film formed on the surface 16 of the stent 10 formed from AA can be between about 20 nm and about 500 nm, for example, between about 70 nm and about 150 nm, such as about 125 nm. The duration of the process of applying the acrylic acid plasma depends on the thickness of the polymer film that is desired to be achieved on the surface 16 of the stent 10. For example, the AA plasma can be applied for about 10 minutes. As indicated by Table 1, carbon dioxide can be also optionally provided with the stream of AA, if it is desirable to limit the rate of de-carboxylation which can occur with an organic acid in a plasma field.

A pulsed plasma, known to those having ordinary skill in the art, can be optionally used for plasma polymerization of AA. If the pulsed plasma is utilized, the process parameters are similar to those of Table 1, except the power range can be between about 80 Watts and about 450 Watts, for example, between about 250 Watts and about 350 Watts. With the pulsed plasma embodiment, the RF power can be pulsed at between about 500 Hz and about 4 kHz, for example, between about 1 kHz and about 1.25 kHz using, for example, a square wave pulse sequence. The duty period (i.e., the time in which the power is on) can be between about 15% and about 100%, for example, between about 20% and about 35%. With the use of pulsed plasma condition, the rate of de-carboxylation can be further limited.

Following deposition of the plasma-polymerized film on the surface 16 of the stent 10, the plasma field can be purged (quenched) with argon without an applied RF field to allow surface free radicals to recombine prior to exposure to atmospheric oxygen. Table 2 provides parameters for the quenching process:

TABLE 2

| Process Parameter | Parameter Range | Exemplary Value |
|---|---|---|
| argon | — | (>99.9% by volume) |
| gas flow rate (sccm) | 30 to 300 | 230 |
| Pressure (mTorr) | 50 to 500 | 250 |
| time (minutes) | 2 to 10 | 3 |

Plasma-induced polymerization using AA yields carboxylated polymers on the surface 16 of the stent 10. The carboxyl groups can be used for the optional conjugating of biocompatible or non-fouling components such as polyethylene glycol, heparin, heparin having hydrophobic counter ions, and superoxide dismutase mimic (SODm).

Optionally, the stent coating can include a region having a drug or therapeutic substance incorporated therein. To form the region having the drug, a polymeric coating impregnated with the drug can be deposited over the plasma-polymerized film. Alternatively, or in addition to being deposed over the plasma-polymerized film, a drug coating can be deposited on the stent and the plasma-polymerized film deposited over the drug coating. To from the drug coating, a polymer can be combined with a therapeutic substance and can be dissolved in a solvent. The solution can be applied onto the stent by any common method, such as spraying or dipping, before and/or after the plasma-polymerized film has been formed. Alternatively, a polymer-free region including the therapeutic substance can be formed, for example, by dissolving the therapeutic substance in a solvent followed by spraying the solution or by dipping the stent in the solution.

Examples of drugs or therapeutic substances that can be used include substances which can inhibit the activity of vascular smooth muscle cells. More specifically, the substance can be aimed at inhibiting abnormal or inappropriate migration and/or proliferation of smooth muscle cells for the inhibition of restenosis. The substance can also include any substance capable of exerting a therapeutic or prophylactic effect for the patient. For example, the substance can be for enhancing wound healing in a vascular site or improving the structural and elastic properties of the vascular site. Examples of therapeutic substances include antiproliferative substances such as derivatives and analogs of actinomycin D (manufactured by Sigma-Aldrich of Milwaukee, Wis.), or COSMEGEN available from Merck & Co. Inc. of Whitehouse Station, N.J. Synonyms of actinomycin D include dactinomycin, actinomycin IV, actinomycin $I_1$, actinomycin $X_1$, and actinomycin $C_1$. The therapeutic substance can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co. of Stamford, Conn.), docetaxel (e.g. Taxotere®, from Aventis S. A. of Frankfurt, Germany) methotrexate, azathioprine, vincristine, vinblastine, fluorouracil, doxorubicin hydrochloride (e.g. Adriamycin® from Pharmacia & Upjohn, of Peapack N.J.), and mitomycin (e.g. Mutamycin® from Bristol-Myers Squibb Co. of Stamford). Examples of such antiplatelets, anticoagulants, antifibrin, and antithrombins include sodium heparin, low molecular weight heparins, heparinoids, heparin derivatives having hydrophobic counter ions, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax made by Biogen, Inc., of Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co. of Stamford), cilazapril or lisinopril (e.g. Prinivil® and Prinzide® from Merck & Co., Inc. of Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., of Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, rapamycin and structural derivatives or functional analogs thereof, such as 40-O-(2-hydroxy) ethyl-rapamycin (known by the trade name of EVEROLIMUS available from Novartis), 40-O-(3-hydroxy)propyl-rapamycin, 40-O—[2-(2-hydroxy)ethoxy]ethyl-rapamycin, 40-O-tetrazole-rapamycin; tacrolimus and dexamethasone.

Embodiments of the present invention have been disclosed with reference to a stent, such as balloon expandable or self-expandable stents. However, other implantable medical devices are also within the scope of the invention. Examples of such implantable devices include stent-grafts, grafts (e.g., aortic grafts), artificial heart valves, abdominal aortic aneurysm devices, cerebrospinal fluid shunts, pacemaker electrodes, and endocardial leads (e.g., FINELINE and ENDOTAK, available from Guidant Corporation). The underlying structure of the device can be of virtually any design. The device can be made of a metallic material or an alloy such as, but not limited to, cobalt chromium alloy (ELGILOY), stainless steel (316L), "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

The features and advantages of the invention can be further illustrated by the following Example.

EXAMPLE

Plasma-induced polymerization of a blend of vinylidene fluoride (VDF) and hexafluoropropene (HFP) was conducted using the assembly shown by FIG. 2, where the plasma apparatus shown in FIGS. 5 and 6 was utilized. A 13 mm VISION stent (available from Guidant Corp.) was coated. The conditions of the plasma polymerization process were as shown in Table 3.

TABLE 3

| Process Parameters | Parameter Value |
| --- | --- |
| VDF flow rate (sccm) | 45 |
| HFP flow rate (sccm) | 45 |
| Pressure (mTorr) | 90 |
| RF power (W) | 80 |
| RF frequency (kHz) | 3.5 |
| Duty cycle, % | 25 |
| Time, min | 5 |

The process of plasma polymerization took about 5 minutes. After the 5 minutes, the plasma was then turned off by terminating the RF power. Microphotographs of the various areas of the stent coating were then made (FIGS. 7-10).

A control stent was coated using the same VDF-HFP blend, under the same conditions as those described in Table 3. However, to coat the control stent, another apparatus was used instead of the apparatus of the present invention. The control apparatus was similar to the apparatus shown by FIGS. 5 and 6, except that in the control apparatus the inner tubular screen 40 was not grounded. Microphotograph of the control stent coating was then made (FIG. 11).

Figure 11:
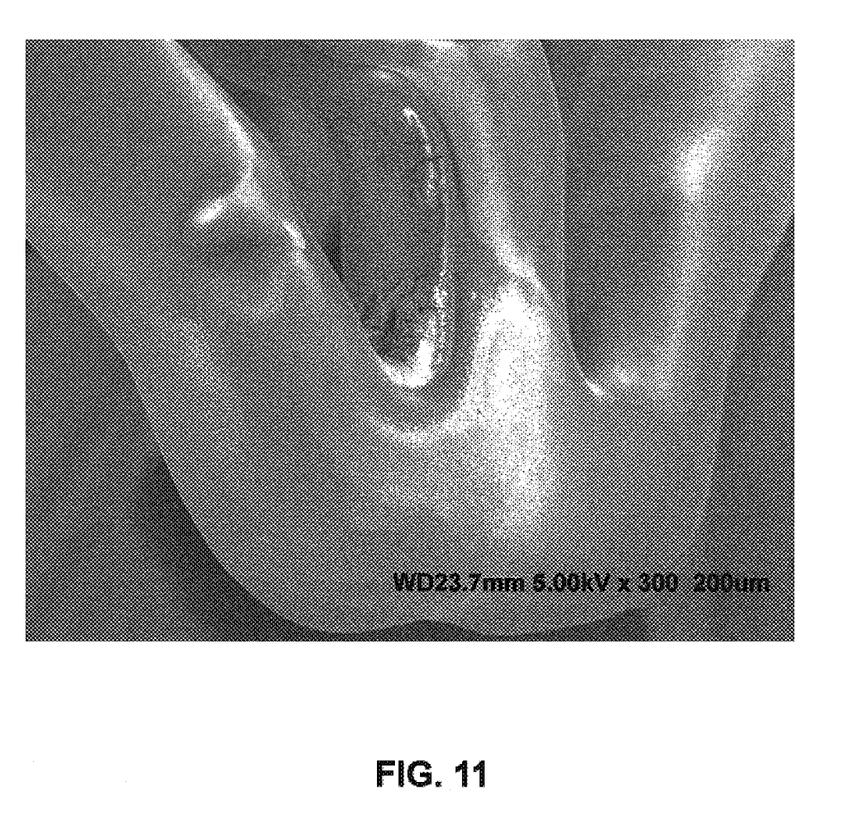
FIG. 11 is a microphotograph of a control stent coating.

By comparing the microphotographs shown by FIGS. 7-10 and by FIG. 11, one can see that the process carried in the apparatus of the present invention leads to much better quality of the stent coating. The coating obtained by the apparatus of the present invention was smooth, uniform and did not have any burn marks. By comparison, the control coating has visible defects.

While particular embodiments of the present invention have been shown and described, it will be obvious to those skilled in the art that changes and modifications can be made without departing from this invention in its broader aspects and, therefore, the appended claims are to encompass within their scope all such changes and modifications as fall within the true spirit and scope of this invention.

What is claimed is:
1. An apparatus to plasma coat a stent, comprising:
a mandrel supporting a stent;
a first plasma member circumscribing the mandrel, the first plasma member being grounded and the mandrel being supported as a cantilever from the first plasma member;

a second plasma member circumscribing the first plasma member;

a plasma generating source in communication with the second plasma member;

a first horizontally disposed plate member in communication with the first plasma member;

a second horizontally disposed plate member positioned over the first plate member and in communication with the second plasma member;

a third plate member, wherein the second plate member is adjacent to, and in communication with a proximal end of the second plasma member and the third plate member is adjacent to, and in communication with a distal end of the second plasma member; and an insulator disposed between the first and second plate members to electrically insulate the plate members;

wherein the mandrel extends from the first plate member into the first plasma member and through an opening formed in the second plate member.

2. The apparatus of claim 1, wherein the first plasma member is a first hollow tubular body in which the mandrel is positioned, and wherein the second plasma member is a second hollow tubular body in which the first hollow tubular body is positioned.

3. The apparatus of claim 2, wherein the first and second hollow tubular bodies include perforations.

4. The apparatus of claim 2, wherein the stent is positioned in the center of the first hollow tubular body.

5. The apparatus of claim 1, wherein the stent does not contact the first plasma member during the coating process.

6. The apparatus of claim 1, wherein the first plasma member is a hollow tubular body in which the mandrel is positioned and wherein the second plasma member is a coil element wrapped around the hollow tubular body.

7. The apparatus of claim 1, wherein the plasma generating source is a radio frequency generating source.

8. The apparatus of claim 1, wherein the plasma generating source generates gaseous plasma to modify a surface of the stent.

9. The apparatus of claim 1, wherein the plasma generating source generates gaseous plasma to form a polymer film on a surface of the stent.

10. The apparatus of claim 9, further comprising a plasma-polymerizable monomer that is in a gaseous form and is inside the second plasma member.

11. The apparatus of claim 10, further comprising a source that supplies the polymerizable monomer gas to the second plasma member.

12. The apparatus of claim 1, wherein the plasma generating source generates gaseous plasma to induce polymerization of a plasma-polymerizable monomer on a surface of the stent to form a polymer film.

13. The apparatus of claim 12, wherein the plasma-polymerizable monomer is in a gaseous form and is inside the second plasma member.

14. The apparatus of claim 13, further comprising a source that supplies the polymerizable monomer gas to the second plasma member.

15. The apparatus of claim 1 wherein a substantial portion of the stent mandrel is disposed between the second and third plate members.

16. The apparatus of claim 1, wherein the mandrel is supported as a cantilever from an end of the first plasma member.

* * * * *